United States Patent
Dicpinigaitis

(12) 
(10) Patent No.: US 6,194,460 B1
(45) Date of Patent: Feb. 27, 2001

(54) COMPOSITION FOR TREATING COUGH INDUCED BY ANGIOTENSIN CONVERTING ENZYME INHIBITORS

(75) Inventor: Peter Dicpinigaitis, Woodhaven, NY (US)

(73) Assignee: Montefiore Medical Center, Bronx, NY (US)

( * ) Notice: Subject to any disclaimer, the term of this patent is extended or adjusted under 35 U.S.C. 154(b) by 0 days.

(21) Appl. No.: 08/456,090

(22) Filed: May 31, 1995

(51) Int. Cl.$^7$ .......................... A61K 31/195; A61K 31/40
(52) U.S. Cl. ............................ 514/567; 514/423; 514/850
(58) Field of Search ..................................... 514/567, 423, 514/850

(56) References Cited

U.S. PATENT DOCUMENTS 5,006,560 * 4/1991 Kreutner et al. ..................... 514/114

OTHER PUBLICATIONS

Bolser et al, Br.J. Pharmacol. (1994),113, 1344–1348.
Bolser et al, Br.J. Pharmacol. (1993) 110, 491–495.
Houston et al., British Journal of Pharmacology, Proceedings Supplement, vol. 112, May 1994, 264p.*

* cited by examiner

*Primary Examiner*—Minna Moezie
*Assistant Examiner*—S. Wang
(74) *Attorney, Agent, or Firm*—Hedman & Costigan, P.C.

(57) ABSTRACT

The claims define a method which is based on the use of baclofen to suppress the cough of a patient who is afflicted with a cough that is induced by the administration of an ACE inhibitor. The usual dose of baclofen is from 10 to 30 mg daily. A pharmaceutical composition which comprises an effective amount of an ACE inhibitor is also disclosed which is a combination of an ACE inhibitor and an amount of baclofen which is effective to suppress the cough which is caused by the administration of the therapeutic dose of an ACE inhibitor.

6 Claims, No Drawings

COMPOSITION FOR TREATING COUGH INDUCED BY ANGIOTENSIN CONVERTING ENZYME INHIBITORS

BACKGROUND OF THE INVENTION

Angiotensin converting enzyme (ACE) inhibitors are widely used in the treatment of hypertension, congestive heart failure, acute myocardial infarction and diabetic nephropathy. One of the side effects that is often observed in patients who are taking ACE inhibitors is a persistent, dry cough that is refractory to most commonly prescribed cough suppressants. The cough is sometimes so severe that therapy with the ACE inhibitor must be discontinued.

Even those patients who respond to conventional cough suppressants are subject to the disadvantages associated with long term use of opiates and other non-opiate cough suppressants.

In the prior art, baclofen has been described as a $GABA_\beta$ agonist which has antitussive effects. Br. J. Pharmacol. (1993)110, 491–495) These effects have been demonstrated by counting the number of coughs elicited during a 4 minute or 30 minute period against capsaicin challenge by subcutaneous administration or by inhalation when baclofen and other antitussives were administered.

The present invention provides a method of suppressing the cough that is observed in patients, who are being maintained on an ACE inhibitor, which comprises the coadministration of baclofen with the ACE inhibitor. Based on the published literature, it was surprising and unexpected that no substantial antitussive effect, which could be attributed to the coadministration of baclofen with the ACE inhibitor, is observed until about three days after the initiation of baclofen therapy.

SUMMARY OF THE INVENTION

The present invention is directed to the coadministration of an amount of baclofen which is effective to suppress the cough of a patient who is afflicted with a cough that is induced by the administration of an ACE inhibitor. The usual dose of baclofen, for the treatment of cough associated with the administration of ACE inhibitors, is from 10 to 30 mg daily p.o. which is given in two to four divided doses. Higher doses may be used, if required in specific circumstances.

The invention also comprises a novel pharmaceutical composition which comprises a therapeutically effective amount of an ACE inhibitor in combination with an amount of baclofen which is effective to suppress the cough which is caused by the administration of the therapeutic dose of an ACE inhibitor.

Generally the composition will contain the usual therapeutic dose of the ACE inhibitor and from 2 to 10 mg of baclofen per oral dosage unit such as a tablet or capsule. If desired, the composition may be formulated as an extended or sustained release dosage formulation which contains a dose of baclofen which is based on the inclusion of a portion of the daily dose of baclofen which would be required over the time period during which the specific type of dosage form will release the ACE inhibitor.

Specific examples of the ACE inhibitors include enalapril, captopril, lisinopril, fosinopril, benazepril, quinapril, alacepril, cilazapril, delapril, enalaprilat, moveltopril, perindopril and ramipril. Persistent dry coughing has been observed as side effect in patients who are treated with these drugs.

The composition of the ACE inhibitor and the baclofen may be prepared using conventional excipients and binders which are well known in the art. For example a tablet may be made which contains 25 mg of captopril, 5 mg of baclofen, microcrystalline cellulose, corn starch, lactose and stearic acid. Other formulations may be prepared using techniques which are disclosed in Remington's Pharmaceutical Sciences, 1985 Ed., Mack Pub. Co., Easton, Pa. which is incorporated by reference.

The following example is added to illustrate the invention. It is not to be construed as a limitation on the invention.

EXAMPLE

A clinical study was carried out in patients who were experiencing coughing that was associated with the administration of ACE inhibitors.

Baseline pulmonary studies confirmed the presence of normal spirometry in four subjects. Two subjects exhibited mild restrictive ventilatory impairment; mild small airways obstruction was seen in one subject. All patients demonstrated normal bronchial responsiveness to inhaled methacholine. The concentration of methacholine ($PC_{20}$) inducing a 20% reduction in forced expiratory volume in one second ($FEV_1$) from baseline was greater than 25 mg/dl in each subject.

All subjects exhibited significant reductions in cough after initiation of baclofen therapy while continuing ACE inhibitor therapy. The patient profiles are summarized in Table 1. The mean time for observing a reduction in coughing is 4.0 days (range 3 to 6 days) The maximum improvement during therapy is achieved at 10.7 days (range 5–15 days). Patients were instructed to subjectively provide a cough score based on the following criteria: base line cough before taking baclofen=3.0; persistent but definite improvement=2.0; mild cough, less than six episodes per day=1.0; and no cough= 0.0. Using this evaluation method, six of the seven patients achieved a cough score of 1 while on therapy; one subject attained a minimal cough score of 1.5. All patients demonstrated a progressive diminution in cough while on therapy except for subject 6 who developed an acute respiratory tract infection characterized by fever and sputum production. This illness transiently elevated the patient's cough score from 1 to 1.5 on days 8–25 of therapy. The cough score returned to 1 by day 26 of treatment. The cough scores are summarized in Table 2.

All subjects experienced persistent suppression of cough after withdrawal of baclofen therapy. Only one subject demonstrated a return to the patients previous baseline cough within 28 days after discontinuation of baclofen. All other subjects did not return to their previous baseline until 35–68 days after cessation of treatment. Two subjects actually showed a transient improvement in cough after discontinuation of baclofen therapy which was followed by the return of a severe cough. The cough Score of patients after the withdrawal of baclofen therapy is shown in Table 3.

All subjects reported compliance with their dosing schedules during the study. No adverse side effects attributable to baclofen were reported or observed during the study.

TABLE 1

| Subject | Age, sex | Diagnosis | ACE inhibitor | dosage (mg) |
| --- | --- | --- | --- | --- |
| 1 | 55,M | CHF,HTN,IDDM | captopril | 25 tid |
| 2 | 73,F | HTN,IDDM | fosinopril | 10 OD |
| 3 | 43,M | HTN | enalapril | 5 bid |
| 4 | 55,M | HTN,NIDDM,MI | enalapril | 15 OD |
| 5 | 61,F | CHF | fosinapril | 15 OD |

TABLE 1-continued

| Subject | Age, sex | Diagnosis | ACE inhibitor | dosage (mg) |
|---|---|---|---|---|
| 6 | 55,F | CHF,HTN | enalapril | 5 bid |
| 7 | 66,F | CHF | captopril | 25 tid |

CHF = congestive heart failure
HTN = hypertension
(N)IDDM = (n0n) insulin-dependent diabetes mellitus
MI = myocardial infarction

TABLE 2

Effect of Baclofen Therapy on Cough Score

| | Number of Days on Baclofen Therapy | | | | |
|---|---|---|---|---|---|
| Subject | 0 | 7 | 14 | 21 | 28 |
| 1 | 3 | 2 | 1 | 1 | 1 |
| 2 | 3 | 2 | 1.5 | 1.5 | 1.5 |
| 3 | 3 | 1 | 1 | 1 | 1 |
| 4 | 3 | 2 | 1 | 1 | 1 |
| 5 | 3 | 2 | 2 | 1 | 1 |
| 6 | 3 | 1 | 1.5* | 1.5* | 1 |
| 7 | 3 | 2 | 1 | 1 | 1 |

*Subject developed acute respiratory tract infection characterized by fever and production of purulent sputum.

TABLE 3

Cough Score After Withdrawal of Baclofen Therapy

| Subject | 7 | 14 | 21 | 28 |
|---|---|---|---|---|
| 1 | 0.5 | 1 | 1 | 2 |
| 2 | 1.5 | 1.5 | 1.5 | 1.5 |
| 3 | 1 | 0 | 0 | 0 |
| 4 | 1 | 1 | 1 | 2 |
| 5 | 1 | 1.5 | 1.5 | 1.5 |
| 6 | 1 | 1 | 2 | 3 |
| 7 | 1 | 1 | 1 | 1 |

The test results show that the use of baclofen to suppress the cough associated with the use of an ACE inhibitor is effective provide the baclofen is administered for a sufficient period of time to allow the baclofen to exert its antitussive effect.

I claim:

1. A pharmaceutical composition which comprises an ACE inhibiting effective amount of an ACE inhibitor and an amount of baclofen which is sufficient to inhibit the cough which is associated with the administration of an ACE inhibitor.

2. A pharmaceutical composition as defined in claim 1 wherein the ACE inhibitor is selected from the group consisting of enalapril, captopril, lisinopril, fosinopril, benazepril, quinapril, alacepril, cilazapril, delapril, enalaprilat, moveltopril, perindopril and ramipril.

3. A pharmaceutical composition as defined in claim 2 wherein the ACE inhibitor is captopril.

4. A pharmaceutical composition as defined in claim 2 wherein the ACE inhibitor is fosinopril.

5. A pharmaceutical composition as defined in claim 2 wherein the ACE inhibitor is enalapril.

6. A pharmaceutical composition as defined in claim 1 wherein the baclofen is present at a level of 2 mg to 10 mg per dosage unit.

* * * * *